United States Patent [19]

Girardeau et al.

[11] Patent Number: 4,867,972

[45] Date of Patent: Sep. 19, 1989

[54] NOVEL SURFACE-ACTIVE COMPOSITIONS CONTAINING POLYDICARBOXYLIC ACID POLYMER AND SURFACTANT

[75] Inventors: Yvette Girardeau, Fontaines-Sur-Saone; Patrick Gaudinet, Miribel; Sylvie Queuche, Fontaines-Sur-Soane, all of France

[73] Assignee: Rhone-Poulenc Specialites Chimiques, Courbevoie, France

[21] Appl. No.: 860,029

[22] Filed: May 6, 1986

[30] Foreign Application Priority Data

May 6, 1985 [FR] France ................................ 85 06827

[51] Int. Cl.⁴ ............................................. A61K 31/78
[52] U.S. Cl. ...................................... 424/81; 424/409; 514/951; 514/952; 524/556; 252/354; 252/351; 252/356; 8/558
[58] Field of Search .................. 424/81, 469; 514/951, 514/952; 524/556; 252/354, 351, 356

[56] References Cited

U.S. PATENT DOCUMENTS

| | | |
|---|---|---|
| 4,191,680 | 3/1980 | Wegmann et al. . |
| 4,267,099 | 5/1981 | Okumichi et al. . |
| 4,309,338 | 1/1982 | Okumichi et al. . |
| 4,460,732 | 7/1984 | Buscall et al. . |
| 4,547,199 | 10/1985 | Boehmke et al. . |

FOREIGN PATENT DOCUMENTS

| | | |
|---|---|---|
| 0077233 | 4/1983 | European Pat. Off. . |
| 0099179 | 1/1984 | European Pat. Off. . |
| 0108302 | 5/1984 | European Pat. Off. . |
| 3004185 | 8/1980 | Fed. Rep. of Germany . |
| 2019822 | 11/1979 | United Kingdom . |

OTHER PUBLICATIONS

Derwent Japanese Patents Report, vol. 75, No. 1, Feb. 4, 1975, p. 2, No. A97-C3-D25-G2.

*Primary Examiner*—Joseph L. Schofer
*Assistant Examiner*—Peter F. Kulkosky
*Attorney, Agent, or Firm*—Burns, Doane, Swecker & Mathis

[57] ABSTRACT

Novel surface-active, storage-stable compositons well adopted for the formulation of a variety of active agents, e.g., biocides, and the conversion thereof into stable, homgenous liquid suspensions, are comprised of at least one first polyolefinic copolymeric surface-active agent (a) and at least one second mixed sulfate and/or phosphate ester surface-active agent (b).

41 Claims, No Drawings

NOVEL SURFACE-ACTIVE COMPOSITIONS CONTAINING POLYDICARBOXYLIC ACID POLYMER AND SURFACTANT

BACKGROUND OF THE INVENTION

1. Field of the Invention:

The present invention relates to novel surface-active compositions which are synergistically active vis-a-vis the individual constituents thereof and to the production of such compositions. The invention also relates to the use of said compositions in the formulation of various active agents in the form of wettable powders or granular materials; it too relates to aqueous or organic dispersions of active materials produced from said wettable powders or granular materials.

2. Description of the Prior Art:

In many fields of use, such as phytopharmacy, the building industries, and the painting and paper, textile, cosmetics, etc., industries, there is a need to prepare aqueous or organic dispersions of active materials, or active agents, which are insoluble or difficult to dissolve in water and which are in finely divided form. By the term "active materials" is intended both pigments and coloring agents, optical bluing agents, additives for plastics and paints, adjuvants for textiles, adjuvants for concretes, cosmetic products, biocidal compounds, more particularly active agents for phytopharmaceutical applications such as herbicides, fungicides, insecticides, acaricides or any other biocidal agent having phytopharmaceutical activity, and the like.

Active materials of such nature, which are employed in the form of suspensions upon actual use thereof may be in the form of wettable powders or in the form of granular materials. Such formulations in most cases include one or more active materials, one or more surface-active agents, fillers and possibly auxiliary substances, or adjuvants.

The active material comprising the formulation is insoluble in water or very difficult to dissolve. It occurs either in solid form or in liquid form. In such latter case, it is necessary for it to be absorbed onto a suitable carrier.

However, having regard to the diversity of active materials having a preponderant hydrophobic character and the nature of the dispersing agent, which in most cases is water, a certain amount of difficulty is involved in selecting a satisfactory surface-active agent. The choice of the surface-active agent is made difficult by the existence of a large number of parameters to be observed.

In order to have a good formulation for the active material, the surface-active agent must not display any incompatibility with the latter and it must present a good binding and film-forming capacity in order to produce granular materials having a very high proportion of active material. It must also be ensured that the active material enjoys a high level of stability in the course of storage and, in particular, the formation of lumps in the wettable powder or the formation of fines in the granular materials must be prevented.

In the preparation of the dispersion of the active material, which is also referred to as "slurry", the surface-active agent must have a good wetting capacity in order to properly wet the active material and a good dispersant capacity in such a fashion that the active material is properly dispersed in the water and the dispersion produced is homogenous and stable for at least the time of application thereof without causing any secondary problems, such as, for example, the formation of foams, or flocculation which may cause blockage of the nozzles of the spraying equipment, and if ever settlement should occur over the course of casual storage prior to use of the materials, it is desirable that the active material revert very easily to the form of a dispersion.

Finally, upon using the material and more particularly in the case of phytopharmaceutical use thereof, the surface-active agent can promote improved availability of the active material: improved wettability of the portions of the plant which are to be treated, and better penetration into the plants.

As will be clearly apparent from the foregoing, it is very difficult to identify a surface-active agent, or a surface-active system, which satisfies all of the requirements outlined above.

French Pat. No. 2,397,444 describes that, in order to prepare stable and concentrated dispersions of active materials in the form of non-dusting powders or granular materials, it is necessary to separate the active material in the presence of a salt of an acidicresin, such as, for example, a copolymer of maleic anhydride and an α-olefinic compound; add an organic solvent which forms, together with the aqueous medium, a two-phase system; treat such two-phase system by adding a carrier substance thereto; and then isolate the product by a reduction in the volume of the organic phase by the addition of water, the solvent gradually transferring into the added water.

It has now been determined that the use of an acidic resin as described above is not entirely satisfactory, particularly when using active materials which are difficult to formulate, because the dispersability thereof is unsatisfactory and flocculation and/or settlement occur between the time of preparation of the slurry and the use thereof in the technical area in question.

SUMMARY OF THE INVENTION

Accordingly, a major object of the present invention is the provision of an improved surface-active system which makes it possible to formulate, from raw materials which are of the greatest possible variety, suspensions which are both stable and homogenous, irrespective of the degree of dilution thereof.

Briefly, the present invention features a novel surface-active composition which comprises:

(1) a surface-active agent (a) comprising at least one copolymer of (i) an unsaturated carboxylic acid or derivative thereof, having the formula (I):

or carboxyl derivative thereof, wherein $R_a$ is a hydrogen atom, an alkyl radical having from 1 to 10 carbon atoms, or a carboxylated such radical, and $R_b$ is a hydrogen atom or a carboxyl group, —COOH, with (ii) an α-olefinic compound having the formula (II) and/or a vinyl compound having the formula (III):

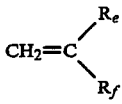

wherein $R_c$ represents a hydrogen atom or a straight or branched chain alkyl radical having from 1 to 4 carbon atoms, $R_d$ represents a straight or branched chain alkyl radical having from 1 to 12 carbon atoms, $R_e$ represents a hydrogen atom or an alkyl radical having from 1 to 4 carbon atoms, and $R_f$ represents one of the following groups:

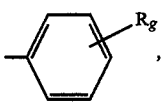

wherein $R_g$ is a hydrogen atom, or one or more alkyl radicals having from 1 to 4 carbon atoms;
—Cl;
—OOC—$R_h$, wherein $R_h$ is an alkyl radical having from 1 to 8 carbon atoms;
—O—$R_i$, wherein $R_i$ is $R_h$;
—COOH;
—COO—$R_j$, wherein $R_j$ is $R_h$;
—CO—NH$_2$; and
—C"N; and (2) a surface-active agent (b) comprising at least one mixed sulfate having the formula (IV) and/or a phosphoric ester having the formula (V):

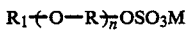

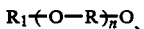

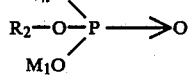

wherein n ranges from 1 to 80, M is an organic or inorganic residue, selected such as to provide the desired solubility, $M_1$ is a hydrogen atom or a residue M, R is an alkylene radical having from 2 to 4 carbon atoms, $R_2$ is either a residue $M_1$ [the two residues $M_1$ (when $R_2=M_1$) may be identical or different], or a radical $R_1$—(O—R)$_{\overline{n}}$ [the radicals $R_2$ and $R_1$—(O—R)$_{\overline{n}}$ may be identical or different], and $R_1$ is a radical having the formula (VI):

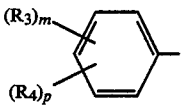

wherein m is an integer equal to 1, 2 or 3; p is an integer equal to 1 or 2; $R_4$ is a hydrogen atom or an alkyl radical having from 1 to 4 carbon atoms and $R_3$ is a radical having the formula (VII):

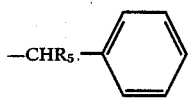

wherein $R_5$ is a hydrogen atom, an alkyl radical having from 1 to 4 carbon atoms, or a phenyl radical.

DETAILED DESCRIPTION OF THE PREFERRED EMBODIMENTS OF THE INVENTION

More particularly according to the invention, the copolymer comprising the surface-active agent (a), referred to simply as the copolymer (a), is basically a known polymer which ha been described in the literature.

Exemplary of the monomers which are typically used in the preparation of the copolymer (a), representative are:

Of the carboxylic acid or derivative thereof: maleic acid or fumaric acid or derivatives thereof, such as esters or hemiesters; itaconic acid and citraconic acid; maleic anhydride; mono- and dialkylmaleic acids and mono- and dialkylfumaric acids, the alkyl radical having from 1 to 4 carbon atoms;

Of the α-olefinic compound: a straight or branched chain unsaturated hydrocarbon containing from 2 to 8 carbon atoms. Specific examples thereof include ethylene, propylene, but-1-ene, isobutylene, n-pent-1-ene, isoprene, 2-methyl-but-1-ene, n-hex-1-ene, 2-methyl-pent-1-ene, 4-methyl-pent-1-ene, 2-ethyl-but-1-ene, 2,4,4-trimethyl-pent-1-ene (referred to as diisobutylene), 1,3-butadiene, 1,3pentadiene, 1,3-hexadiene, 1,3-octadiene, 2-methyl-3,3-dimethyl-pent-1-ene and 2-methyl-4,4-dimethyl-pent-1-ene;

Of the vinyl compound: styrene, vinyl chloride, vinyl esters of aliphatic acids having from 1 to carbon atoms, such as vinyl acetate, vinyl propionate, vinyl butyrate, vinyl ethers, such as methyl and vinyl oxide, acrylic or methacrylic acid, and their alkyl esters containing from 1 to 8 carbon atoms, such as methyl, ethyl or butyl acrylate, methyl, ethyl and butyl methacrylate, acrylamide, methacrylamide, acrylonitrile and methacrylanitrile.

A copolymer of maleic anhydride with diisobutylene is the most preferred polymer (a).

The proportion of the monomers to be used is such that the molar ratio of unsaturated carboxylic acid of the formula (I) to the unsaturated compounds of the formula (II) and/or (III) is approximately 1 and preferably is indeed equal to 1.

The preferred copolymers (a) are those which have a mean molecular weight of from 500 to 50,000 and preferably from 500 to 15,000.

These are produced by radical polymerization in a solvent, such as, for example, benzene, toluene, xylene, dioxane, ethyl acetate or possibly the α-olefinic or vinyl compound which is used in substantial excesses.

The catalysts generating free radicals which are suitable for the invention are in most cases peroxides or hydrperoxides azo compounds, such as, for example, acetyl peroxide, di-tert-butyl peroxide, benzoyl peroxide, lauroyl peroxide, tert-butyl perbenzoate, methyl hydroperoxide, ethyl hydroperoxide, tert-butyl hydroperoxide, cumene hydroperoxide, azodiisobutyronitrile and dimethyl azoisobutyrate.

The catalyst may be used in a proportion of from 0.3 to 5% of the weight of the monomers involved.

The polymerization temperature is preferably selected at from 60° C. to the boiling point of the reaction medium.

The copolymer (a) is obtained in an organic solution. It may optionally be neutralized by the addition of base, until the pH ranges from 8 to 12. Bases which are suitable include sodium hydroxide, potassium hydroxide, lime, ammoniac, ammonia, or a quaternary ammonium hydroxide, for example, trimethylbenzylammonium hydroxide.

The optionally neutralized copolymer (a) is transferred into an aqueous solution by the addition of water and then distillation of the organic solvent.

The aqueous solution of copolymer (a) may contain up to 25% by weight of dry solids.

Another form in which the surface-active agent (a) exists is the powder form. It is possible, for example, to carry out the drying operation in an atomization tower by spraying the aqueous solution which has been previously produced into a stream of air, whose intake temperature ranges from 140° to 240° C.

As surface-agents (a) which are commercially available, a maleic anhydride/diisobutylene copolymer is exemplary, for example, marketed by RHONE-POULENC or by GERONAZZO under the trademarks SOPROPON T 36, SOPROPON T 36 K or GEROPON TA 72.

The use of a mixture of surface-active agents (a) is well within the scope of the invention.

Concerning the surface-active agent (b), preferred are the compounds of the formulae (IV) and (V), in which n ranges from 1 to 40, M is an ammonium residue or an alkali metal atom, and $M_1$ is a hydrogen atom, an alkali metal atom or an ammonium residue.

By the term "ammonium residue" is intended a compound of the formula N ($R_6$, $R_7$, $R_8$, $R_9$) in which $R_6$ is a hydrogen atom, and $R_7$, $R_8$ and $R_9$, which are identical or different, are each hydrogen, or an alkyl or hydroxyalkyl radical, with the proviso that two of the alkyl radicals may together form a single divalent radical optionally containing a bridging oxygen atom; the total number of carbon atoms in the ammonium residue is less than or equal to 6.

Further, R represents an ethylene radical, $R_1$ represents a radical of the formula (VI) in which m is a number equal to 2 or 3; $R_4$ is a hydrogen atom; $R_3$ is a radical of the formula (VII)

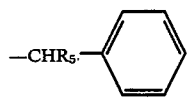

(VII)

in which $R_5$ is a hydrogen atom, or a methyl or phenyl radical, and $R_2$ is either a residue $M_2$ [the two residues $M_1$ being identical when $R_2=M_1$] or a radical $R_1$—(O—CH$_2$)$_{\overline{n}}$ [the radicals $R_2$ and $R_1$—(O—CH$_2$—CH$_2$)$_{\overline{n}}$ being identical].

In the preferred group of surface-active agents (b), particularly suitable for the invention are the surface-active agents of the formulae (IV) and (V) in which n ranges from 3 to 40, M is a sodium or potassium atom, an ammonium radical, a monoethanolamine, a diethanolamine or a triethanolamine, $M_1$ is a hydrogen atom or an M residue, R is an ethylene radical, $R_1$ represents a radical of the formula (VI) in which m is a number equal to 2 or 3; $R_4$ is a hydrogen atom; the radical $R_3$ is a radical of the formula:

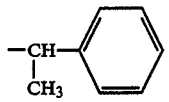

$R_2$ is either a residue $M_1$ [the two residues $M_1$ being identical when $R_2=M_1$] or a radical $R_1$—(O—CH$_2$—CH$_2$)$_{\overline{n}}$ [the radicals $R_2$ and $R_1$—(O—CH$_2$—CH$_2$)$_{\overline{n}}$ being identical].

The surface-active agents which are the preferred are the following:

A - Sulfates of tri-(1-phenyl ethyl)phenols in polyoxyethylenated form, having from 10 to 40 moles of ethylene oxide (E.O.) per mole of phenol, in acid or neutralized form, B - Sulfates of di-(1-phenyl ethyl)phenols, in polyoxyethylenated form, having from 3 to 20 moles of ethylene oxide per mole of phenol, in acid or neutralized form, C - Phosphates of tri-(1-phenyl ethyl)phenols, in polyoxyethylenated form, having from 10 to 40 moles of ethylene oxide per mole of phenol, in acid or neutralized form, D - Phosphates of di-(1-phenyl ethyl)phenols in polyoxyethylenated form, having from 3 to 20 moles of ethylene oxide per mole of phenol, in acid or neutralized form.

The various surface-active agents referred to above are known and commercially available materials. They are marketed, for example, by RHONE-POULENC under the respective trademarks:

A—SOPROPHOR 4 D 384 (16 E.O., acid form),
B—SOPHOPHOR DSS 5 (5 E.O.), DSS 7 (7 E.O.) DSS 11 (11 E.O.),
DSS 15 (15 E.O.) (acid or neutralized form),
C—SOPHOPHOR 3 D 33 (16 E.O.,acid form), FL (16 E.O., neutralized form),
D—SOPHOPHOR 10 D 12/5 (5 E.O.), 10 D 12/7 (7 E.O.), 10 D 12/11 (11 E.O.), 10 D 12/15 (15 E.O.) (acid or neutralized form).

It will be appreciated that it is possible to use the sulfates of formula (IV) separately or as a mixture. The phosphates of formula (V) may be used separately or more generally in the form of mixtures of monoester with the corresponding diester.

It is also well possible to use a mixture of sulfate(s) of the formula (IV) and phosphate(s) of the formula (V), as the surface-active agent (b).

The surface-active compositions of the present invention may be prepared by different processes depending on whether they exist in liquid form or in solid form.

One particular process for the preparation of the surface-active composition of the invention in liquid form consists of heating the surface-active agent (b) and proceeding to a mixture of the surface-active agent (b) and the aqueous solution of the surface-active agent (a).

In a first step, the surface-active agent (b) is heated to a temperature of from 40° to 60° C. It is preferable to use a temperature which is lower than 60° C.

The solution of surface-active agent (a) is introduced into the molten surface-active agent (b), or viceversa. The mixing operation is therefore carried out under hot conditions and with agitation which is produced by conventional agitation means (screw, frame, etc., type agitator).

Another form of the composition of the invention is as a powder. Various methods for the preparation thereof are suitable.

It is possible to carry out the drying operation, for example, in an atomization tower, by spraying the aqueous solution which has previously been produced into a stream of air whose intake temperature ranges from 140° C. to 240° C.

It is also possible to atomize solely the solution of surface-active agent (a) and then to mix the powder obtained with the surface-active agent (b), which is absorbed on a carrier which is compatible with the intended final use thereof.

In every situation, the product is recovered in the form of a powder which is perfectly stable when stored and which is highly suitable for a variety of end uses.

The respective amounts of the two constituents (a) and (b), expressed in terms of weight of dry materials in the compositions of the invention, may vary over wide limits.

The may contain:
from 10 to 90% by weight of one or more surface-active agents (a),
from 90 to 10% by weight of one or more surface-active agents (b).

More precisely, the proportions of the surface-active agents (a) and (b) depend upon the intended use of the surface-active composition and the qualities required thereof.

In order to produce a surface-active composition which is essentially wetting in nature, the following are preferably used:
from 10 to 30% by weight of one or more surface-active agents (a),
from 70 to 90% by weight of one or more surface-active agents (b).

In order to provide a surface-active composition which is predominantly binding and/or dispersing in character, the following are preferably used:
from 80 to 90% by weight of one or more surface-active agents (a),
from 10 to 20% by weight of one or more surface-active agents (b).

The surface-active composition of the invention is particularly well suited for the formulation of active materials which are required to be placed into suspension upon application thereof.

As above mentioned, the active material or materials must be insoluble in water or difficult to dissolve in water at ambient temperature, which is most often between 15° and 25° C.

By the expression "difficult to dissolve" is intended a degree of solubility of less than about 1% by weight.

As active materials which are capable of being formulated in accordance with the invention, exemplary are pigments and fillers, coloring agents, optical bluing agents or various additives in various industries, such as plastics, paints, textile, concrete, cosmetics, etc.

A significant area of use of the invention is in the field of phytopharmacy and more especially the formulation of active materials such as insecticides and acaricides, fungicides and the various associations thereof, herbicides, nematicides, attractants, repellents, and rodenticides.

Exemplary of the insecticides and acaricides which are suitable according to the present invention, representative are those of the following families:

Organohalogenated or chlorinated agents, such as, for example, D.D.T. [dichloro diphenyl trichloroethane], lindane [γ-isomer of hexachlorocyclohexane], chlordane [octachlorotetrahydromethano indene], toxaphene;

Carbinols, such as, for example, dicofol [dichlorophenyl trichloroethanol];

Organophosphorated materials, such as, for example, bromophos [O-(4-bromo-2,5-dichlorophenyl) O,O-dimethyl phosphorothioate], diazinon [O,O-diethyl O-2-isopropyl-6-methyl-4-pyrimidinyl phosphorothioate], fenitrothion [O,O-dimethyl O-4-nitro-m-tolyl phosphorothioate], malathion [S-1,2 bis (ethoxycarbonyl) ethyl O,O-dimethyl phosphorodithioate], parathion [O,O-diethyl O-4-nitrophenyl phosphorothioate], trichlorfon [dimethyl 2,2,2-trichloro-1-hydroxyethylphosphonate], and dimethoate [O,O-dimethyl S-methylcarbamoylmethyl phosphorodithioate];

Sulfones and sulfonates, such as, for example, tetradifon [tetrachloro diphenylsulfone];

Carbamates, such as, for example, carbaryl [N-naphthyl-methyl carbamate], methomyl [N-(methylthio ethylidene amine) methyl carbamate];

Benzoyl ureas, such as, for example, diflubenzuron [difluoro benzoyl chlorophenylurea];

Synthetic pyrethrinoids;

Acaricides, such as, for example, cyhexatin [tricyclohexylhydroxystannane].

Representative of the fungicides which can be used according to the invention are:

Carbamates, such as, for example, benomyl [methyl butylcarbamoyl benzimidazoyl carbamate], carbendazime [methyl benzimidazolyl carbamate], ziram [zinc dimethyl dithiocarbamate], maneb [manganese ethylene bis dithiocarbamate], mancozeb [zinc and magnesium ethylene bis dithiocarbamate], thiram [bis dimethyl thiocarbamoyl disulfide;

Derivatives of benzene, such as, for example, PCNB [pentachloronitrobenzene];

Derivatives of phenol, such as, for example, dinocap [(methylheptyl) dinitrophenyl crotonate];

Quinones, such as, for example, dithianon [dioxodihydro naphtho dihiine dicarbonitrile];

Dicarboximides, such as, for example, captan [trichloromethylthio tetrahydroisoindolinedione], folpel [trichloromethylthio isoindolinedione], and iprodione [dichlorophenyl isopropyl carbamoyl dichlorophenylhydantoine];

Amines and amides, such as, for example, benodanil [iodobenzanilide], and methylaxyl [methyl dimethylphenyl methoxyacetyl alalinate];

Diazines, such as, for example, pyrazophos [thiophosphate of ethyl and ethoxycarbonyl methyl pyrazolo pyrimidine], and fenarimol [chlorophenyl pyrimidine methanol];

Sulfamides and sulfur-bearing derivatives, such as, for example, dichlorofluanide [dichloro fluoro methylthiodimethyl phenyl sulfamide];

Guanidines, such as, for example, doguadine [dodecylguanidine acetate];

Heterocycles, such as, for example, etridiazole [ethoxy trichloromethyl thiadiazole], and triadimefon [chlorophenoxy dimethyltriazol butanone];

Metallic monoethyl phosphites, such as, for example, phosethyl-Al [aluminum tris-O-ethyl phosphonate]; and Organostannic materials, such as, for example, fentine-acetate [triphenyl tin].

An representative of chemical substances having herbicidal properties, also suitable for use according to the invention, are:

Phenol compounds, such as, for example, dinoseb [dinitrobutylphenol];

Carbamates, such as, for example, phenmediphame methyl tolylcarbamoyloxyphenyl carbamate];

Substituted ureas, such as, for example, neburon [butyl dichlorophenyl methyl urea], diuron [dichlorophenyl dimethyl urea], and linuron [dichlorophenyl methoxymethyl urea];

Diazines, such as, for example, bromacil [bromobutyl methyl uracile], and chlorodizone [phenylamino chloropyridazone];

Triazines, such as, for example, simazine [chloro bis-ethylamino s-triazine], atrazine [chloroethylamino isopropylamino s-triazine], terbutylazine [chloroethylamino butylamino s-triazine], terbumeton [tert-butylamino ethylamino methoxy triazine], prometryne [methylthio bis isopropylamino s-triazine], ametryne [methylthio ethylamino isopropylamino s-triazine], metribuzine [methylthio butylaminotriazine-one, and cyanazine [chloro ethylamino s-triazine ylamino methyl propionitrile];

Amides, such as, for example, napropamide [naphthoxy diethyl propionamide], and propachloro [isopropyl chloroacetanilide];

Quaternary ammoniums;

Benzonitriles;

Toluidines, such as, for example, ethalfluraline [dinitroethylmethyl propenyl trifluoro methylaniline], and oryzalin dinitrodipropyl sulfanilamide];

Triazoles;

Various derivatives, such as, for example, benazoline [chloro oxo benzothiazoline acetic acid, dimefuron [chloro oxo tert-butyl oxadiazoline phenyl dimethyl urea], bromophenoxime [dibromo hydroxy dinitro phenyl benzaldoxime], and pyridate [chloro phenyl pyridazinyl carbothiolate octyl].

As other examples of biocides which can be used in accordance with the invention, representative are the nematicides, molluscicides, etc.

It is possible to use one or more active materials belonging to the same class of biocides or to a different class.

A preferred use of the surface-active composition of the invention is in the formulation of the aforementioned active materials in the form of wettable powders or granular materials.

The wettable powders which are produced in accordance with the invention are typically comprised of:

(1) At least one active material, (2) At least the surface-active composition of the invention, (3) Optionally a filler, and (4) Optionally, auxiliary or adjuvant materials.

The active materials, the nature of which has been set forth hereinbefore, exists in solid or liquid state.

The solid active material is in most cases subjected to a crushing operation in order to adjust it to the desired granulometry which is such that 95% by weight of the particles have an apparent diameter of less than 20 μm and the mean diameter ranges from 2 to 10 μm. The mean diameter is defined as a diameter such that 50% by weight of the particles have a diameter which is larger or smaller than the mean diameter.

Account must be taken of the melting point, in regard to the crushing process selected: air jet crushing is preferable when working with active materials having a low melting point (<150° C.). The melting point also has an effect on the possible level of concentration of the active materials. That level may be increased in proportion to a rising melting point.

If the active material is in the liquid state, it is entirely possible for it to be absorbed onto a powdery carrier in orderto present it in solid form.

Preferred for this purpose are the precipitated silicas having a high absorption capability (for example, ZEOSIL 39 A marketed by Rhone-Poulenc) which are used in a sufficient amount to produce a dry powder, or else calcium silicates.

The surface-active composition is in solid or liquid form. In that case, it may also be absorbed onto a carrier.

The fillers are inert compounds which may serve:

(i) either as a carrier for the active material and the surface-active composition of the invention, if they are liquid, (ii) or as an agent for diluting the active material.

There ar crushed natural products suitable for this purpose, such as kaolin, attapulgite, bentonite, chalk, talc, or synthetic materials such as precipitated silica, pyrogenic silica, calcium carbonate, and the like.

With respect to the selection of the fillers, the following characteristics should be borne in mind:

Fineness: this characteristic has a very great influence on the amount in suspension and flow;

pH-value: it is important for the pH of the filler to be suited to the active material, the stability of which is often dependent upon that factor;

Proportion of free water: it is in most cases desirable for the proportion of free water to be as low as possible, degradation of the active materials generally being promoted by the presence of water;

Anti-lumping property: this property is particularly important in regard to wettable powders at a high level of concentration or which are produced from active materials having a low melting point; and Cost: this factor is obviously of an importance which increases in proportion to a decreasing concentration of active materials in the formulation.

Besides the active material, the surface-active composition and at least one diluent filler, auxiliary products can also be used, more specifically:

Foam inhibiting agents which are intended to control the formation of foams upon preparation of the treatment slurry, such as, for example, polysiloxanes;

Anti-lumping agents, for example, fillers of precipitated silica type;

Anti-static agents which may be inorganic salts, such as lithium chloride, or organic phosphates, such as phosphates of fatty alcohols or fatty acids, in particular the potassium salt of tridecylphosphoric acid;

Protective agents which permit stabilization of the active material with respect to oxidation, UV-radiation and variations in pH (buffers); and Various other additives such as coloring agents or adjuvants which are intended to modify adhesion of the treatment slurry to plants, etc.

In the case of particularly hydrophobic active materials, it is advisable to add a wetting agent which will be selected depending upon the crude active material or materials. The choice will preferably be of an anionic or non-ionic surface-active agent. In regard to selecting the surface-active agent, reference may be made, inter alia, to "ENCYCLOPEDIA OF CHEMICAL TECH- NOLOGY", Kirk OTHMER, volume 19, or the different works from the Surfactant Sciences Series, Marcel DEKKER Inc., volume 1: Nonionic Surfactants, by Matin J. SCHICK; volume 7: Anionic Surfactants by Warnier M. LINFIELD, or to the text, McCUTCHEON'S: Detergents and Emulsifiers - International and North American Edition.

The following are exemplary of the anionic surface-active agents:

Soaps of alkali metals, such as sodium or potassium salts of saturated or unsaturated fatty acids having from 8 to 24 carbon atoms, and preferably from 14 to 20 carbon atoms, or derivatives of aminocarboxylic acids, such as sodium N-laurylsarconisate and sodium N-acylsarconisate;

Alkaline sulfonates, such as alkylsulfonates, arylsulfonates or alkylarylsulfonates, in particular alkylsulfonates, such as, for example, diesters of sulfosuccinic acid, such as sodium diethylhexylsulfosuccinate, sodium di-octylsulfosuccinate, and alkylbenzenesulfonate of the formula $R'_1$—$C_6H_4$—$SO_3M'_1$ in which the radical $R'_1$ is a straight or branched chain alkyl radical containing from 8 to 13 carbon atoms, such as, for example, a nonyl, dodecyl or tridecyl radical, and $M'_1$ represents a sodium or potassium atom, an ammonium radical, diethanolamine, triethanolamine or N-methylcyclohexylamine; alkylnaphthalenesulfonates of the formula:

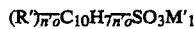
$(R')_{\overline{n'_0}}C_{10}H_{7\overline{n'_0}}SO_3M'_1$ in which $n'_o$ is a number varying from 1 to 3 and the radical $R^1$ is a straight or branched chain alkyl radical containing from 1 to 4 carbon atoms, such as, for example, a methyl, isopropyl or isobutyl radical, and $M'_1$ is as defined above. Other sulfonates may be employed, such N-acyl, N-alkyltaurates of the following formula:

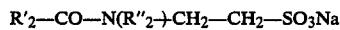
$R'_2$—CO—N($R''_2$)—$CH_2$—$CH_2$—$SO_3Na$ in which $R'_2$ is an alkyl radical having from 11 to 18 carbon atoms and $R''_2$ is a methyl or ethyl radical, such as, for example, sodium N-oleyl, N-methyltaurate or N-palmitoyl, N-methyltaurate; sulfonated olefins resulting from the sulfonation of straight-chain $C_{14}$ to $C_{18}$ olefin cuts;

Sulfates and sulfated products; among the alkyl sulfates corresponding to the formula:

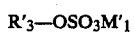
$R'_3$—$OSO_3M'_1$ exemplary are those in which the radical $R'_3$ is a lauryl, cetyl or myristyl radical and $M'_1$ is as defined above; sulfated natural greases and oils; the disodium salt of sulfated oleic acid; polyoxyethylenated and sulfated fatty alcohols having the following formula:

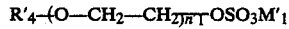
$R'_4$—(O—$CH_2$—$CH_2)_{\overline{n'_1}}$—$OSO_3M'_1$ in which the radical $R'_4$ is an alkyl radical containing from 6 to 16 carbon atoms, such as, for example, a myristyl radical or a straight or branched-chain alkyl radical, such as, for example, a hexyl, octyl, decyl or dodecyl radical, $n'_1$ is the number of ethylene oxide moles, which may vary from 1 to 10, and $M'_1$ is as defined above; sulfated alkyl phenols having the following formula:

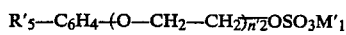
$R'_5$—$C_6H_4$—(O—$CH_2$—$CH_2)_{\overline{n'_2}}OSO_3M'_1$ in which the radical $R'_5$ is a straight or branched-chain alkyl radical containing from 8 to 13 carbon atoms, such as, for example, an octyl, nonyl or dodecyl radical, $n'_2$ is the number of moles of ethylene oxide which may vary from 1 to 20 and $M'_1$ is also as defined above;

Alkaline phosphates; mono- or diesters of orthophosphoric acid or one of the salts thereof which may be represented in regard to alkyl phosphates by the formula:

$(R'_6O) PO (OM'_2)$ and in regard to dialkyl phosphates, by the following formula:

$(R'_6O)_2 PO (OM'_2)$ in which the radical $R'_6$ is a straight or branched-chain alkyl radical containing from 6 to 12 carbon atoms and $M'_2$ represents a hydrogen, sodium or potassium atom. Examples of the radical $R'_6$ that are representative are n-hexyl, n-octyl, n-ethylhexyl, dimethylhexyl, n-decyl, dimethyloctyl, trimethylheptyl, trimethylnonyl; mono- or diesters of orthophosphoric acid or one of the salts thereof, which are polyoxyethylenated, that may be represented in regard to the polyoxyethylenated alkyl phosphates by the formula:

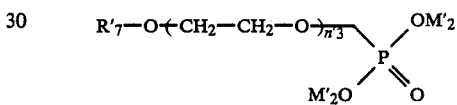

and in regard to the polyoxyethylenated dialkyl phosphates, by the following formula:

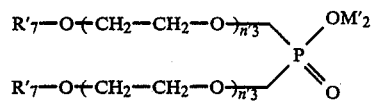

in which the radical $R'_7$ represents a straight or branched-chain alkyl radical having from 6 to 12 carbon atoms, a phenyl radical, or an alkylphenyl radical with an alkyl chain having from 8 to 12 carbon atoms, $n'_3$ is the number of moles of ethylene oxide which may vary from 2 to 20 and $M'_2$ is as defined above. Examples of the radical $R'_7$ that are representative are the hexyl, octyl, decyl, dodecyl, tridecyl and nonylphenyl radicals.

Exemplary of the non-ionic surface-active agents, representative are the compounds which are produced by condensation of alkylene oxide with an organic compound which may be aliphatic or alkylaromatic. Suitable non-ionic surface-active agents are as follows:

Polyoxyethylenated alkylphenols, for example, the products of condensation of ethylene oxide in a proportion of from 5 to 30 moles per mole of alkylphenol, the alkyl radical being straight or branched-chain and containing from 6 to 12 carbon atoms. Preferred are nonylphenol condensed with about 10 to 30 moles of ethylene oxide per mole of phenol, dinonylphenol condensed with 15 moles of ethylene oxide per mole of phenol and dodecylphenol condensed with 12 moles of ethylene oxide per mole of phenol;

Polyoxyethylenated aliphatic alcohols resulting from the condensation with ethylene oxide in a proportion of from 3 to 30 moles of ethylene oxide, of straight or branched-chain fatty alcohols containing from 8 to 22 carbon atoms; for example, the product of condensation of about 15 moles of ethylene oxide with 1 mole of tridecanol or coprah alcohol, or myristyl alcohol condensed with 10 moles of ethylene oxide;

Fatty amides, such as, for example, diethanolamide of fatty acids which are optionally polyoxyethylenated. Coconut oil or lauric acid are specific examples of fatty acids;

Polyoxyethylenated and polyoxypropylenate derivatives; an illustration of this type of surface-active agents are the well-known materials which are marketed under the trademarks "PLURONICS" and "SOPROFOR". These are prepared by the sequential addition of propylene oxide and then ethylene oxide to a reactive hydrogen compound having a low molecular weight, such as, for example, propylene glycol.

Preferably, the following surface-active agents are used: sodium alkylarylsulfonates, sodium diisopropylnaphthalene sulfonates, polyoxyethylenated and sulfated fatty alcohols nd polyoxyethylenated nonylphenols.

The aforementioned surface-active agents are in solid or liquid form. In the latter case, they may also be absorbed, like the surface-active composition of the invention, onto a powdery carrier.

The different constituents referred to above occur in the wettable powders in proportions which may be variable:

(i) from 10 to 90% of active material or materials,
(ii) from 0.5 to 20% of the surface-active composition of the invention,
(iii) from 9.5 to 75% of filler or fillers,
(iv) from 0 to 5% of wetting agent or agents,
(v) from 0 to 5% of auxiliary product or products.

The mode of production of the wettable powders differs depending upon whether the active material is solid or liquid.

When the active material is solid, it will be mixed with the other constituents, such as the surface-active composition of the invention, and the wetting agent which will be absorbed beforehand on an absorbent filler, if they are liquid.

A diluent filler and optionally auxiliary materials may be added to the mixture. The various constituents may be added simultaneously or successively, and there is no critical order.

The mixing time depends on the equipment used and is readily determined by one skilled in this art such that a homogenous mixture is produced.

The mixing operation may be carried out in a powder mixer of known type: free-fall mixers of the drum type, vertical or horizontal mixers of helicoidal screw type, planetary mixers, horizontal mixers of Lodige type, etc.

When the active material is liquid, it is sprayed onto an absorbent filler. It may be advantageous to slightly heat the active material, if its viscosity is high at ambient temperature.

The operation then comprises adding the surface-active composition and the wetting agent simultaneously with the active material, if they are in the liquid state, or after spraying if they are in a solid form or if they are absorbed onto a filler.

A diluent filler and optionally any auxiliary materials may also be added. The mixing operation is continued until the mixture is homogenous. The apparatus used for carrying out this operation is of the same type as the mixers described above.

The wettable powders which are obtained utilizing the composition of the invention display excellent storage stability.

Another embodiment of the surface-active composition of the invention is in the formulation therewith of active material or materials in the form of granules. The granular materials are produced by the agglomeration of an active material with dispersant and binding agents.

The composition of such granular materials is as follows:

(i) At least one active material,
(ii) At least the surface-active composition of the invention,
(iii) Optionally, a wetting agent,
(iv) Optionally, filler material,
(v) Optionally, a disintegrating agent, and
(vi) Optionally, auxiliary products.

The nature of the constituents has been specified above, except as regards the disintegrating agents, the function of which is to assist the liberation of the active material and which may be bentonite, corn starch or highly soluble inorganic salts, such as, for example, sodium bicarbonate or sodium chloride.

The proportions of the various constituents of the granular materials are set forth below:

From 10 to 95% of active material or materials,
From 5 to 20% of the surface-active composition of the invention,
From 0 to 75% of filler or fillers,
From 0 to 5% of wetting agent or agents,
From 0 to 5% of disintegrating agent or agents.

The granular materials of the invention are produced utilizing conventional granulation processes:

Fluidized bed,
Atomization,
Granulation on a rotary plate,
Extrusion,
Various agglomeration processes.

Different modes of preparation of the granular materials are set forth below, illustrating the various granulation procedures; these are not intended to be in any way limiting and are provided solely for purposes of illustration.

Preparation of granular materials on a fluidized bed involves producing a pre-mixture of the solid active material (crushed or absorbed onto a carrier) with all of a part of the surface-active composition of the invention used, in solid form, optionally a wetting agent, and a disintegrating agent, and then spraying onto said pre-mixture an aqueous solution containing all or a part of the surface-active composition of the invention in liquid form, and optionally a liquid wetting agent.

The material is maintained in the fluidized state by means of a rising stream of hot air at a temperature of from 20° to 80° C.

The percentage of water (which in most cases represents 30 to 60% of the filler), the rate of spraying and the rate of air flow must be adjusted to provide optimum levels of performance.

When the granular materials are formed, they may be dried in the same equipment by means of a stream of hot air which is at a temperature lower than the melting or decomposition temperature of the active material.

It is also envisaged to spray into the fluidized bed a slurry containing the crushed active material, the surface-active composition and optionally the wetting agent, both preferably in liquid form. The slurry may contain from 50 to 75% of dry solids. In that case, it is necessary to commence the operation utilizing an amount of seed granules, which are taken from a previous production.

The size of the granules may vary over fairly wide limits, of from 0.1 to 2 mm.

In accordance with another embodiment of the invention, the granules may be prepared by atomization, if the melting temperature of the active material permits same.

A concentrated slurry containing the active material, the surface-active composition of the invention, optionally the wetting agent, the disintegrating agent and the various adjuvants, if necessary, is sprayed into a stream of hot air between 140° and 240° C. The slurry is concentrated (the dry extract thereof is from 50 to 70%) and it has a viscosity of from 300 to 1000 mPa.s.

The atomization is carried out by spraying in the form of large drops, preferably using bi-fluid nozzles.

Upon completion of the atomization procedure, a dry product is generally obtained.

If that is not the case, it is possible to carry out a complementary drying operation using any suitable means, drying with air or under reduced pressure which is effected, for example, in an oven, or drying in a fluidized bed, etc.

The size of the granules obtained generally varies between 100 and 500 μm.

Another manner of carrying out this embodiment of the invention consists of agglomerating the active material on a rotary plate.

The solid materials such as active material, surface-active composition of the invention, filler, auxiliary products, etc., are charged onto the rotary plate and the mixture thereof is homogenized by rotary movement of the plate.

For purposes of agglomeration of the active material, water spraying is carried out, optionally with the addition of a wetting agent or a fraction of the surface-active composition of the invention in liquid form.

The percentage of water generally varies from 7 to 15%.

The granules which are produced in such manner must be dried in a second step until the proportion of water is from 0.3 to 1%, depending on the active material.

The drying operation is carried out at a temperature which is lower than the melting or decomposition temperature of the active material. It may be carried out using air, or under reduced pressure, as described hereinbefore.

The granules are more or less spherical in shape and they vary in size from 100 and 500 μm.

Another embodiment of the invention also consists of granulating the active material, bu using an extrusion process.

In a first step, a powder-to-powder mixture is typically produced, using the active material which is in crushed form or on a carrier, the surface-active composition of the invention in solid form, fillers and other additives in solid form.

The mixture obtained is moistened by addition thereto of from 10 to 30% by weight of water. The water may be added by spraying. It is also possible to add a wetting agent thereto, or all of a part of the surface-active composition of the invention in liquid form.

The mixture of constituents is produced in a powder mixer of known type, as referred to hereinbefore.

Extrusion of the resulting paste is then carried out, generally in an apparatus which operates at low pressure. After extrusion, the granules must be dried. The drying operation does not require any special technique.

It would not be a departure from the scope of the present invention for the granulation operation to be carried out using other processes.

It is possible to carry out the agglomeration operation using other processes which entail spraying water onto a dry mixture of active material, the surface-active composition of the invention, fillers and various additives.

The mixture is maintained in a state of movement by mechanical means. It is possible to use different forms of chambers and agitation systems. It is possible to employ a SCHUGI mixer or a double-casing turbosphere apparatus from MORITZ.

Another embodiment of the process of the invention consists of separately using the surface-active agent (a) and the surface-active agent (b) which comprise the surface-active composition of the invention: the agents (a) and (b) which are either in liquid or solid form may be introduced at different stages in the formulation procedure, irrespective of the manner of producing the wettable powder or irrespective of the granulation procedure involved.

It may be advantageous to utilize this particular embodiment of the invention, as it permits the levels of performance of the formulation in the case of certain active materials to be optimized.

The wettable powders and the granular materials comprising the surface-active composition of the invention are readily placed into the form of a dispersion upon end use thereof. The dispersion medium may be an organic solvent, but in most cases it is water.

Production of the treatment slurry is done simply by adding the wettable powder or the granules to the dispersion medium, which may be agitated manually, or by means of a conventional agitation system (agitation by means cf an armature-type system, a screw-type system, a turbine-type system, etc.). That type of agitation is most frequently superfluous and may be attractive only when the amounts of active material to be used are substantial.

The wettable powders produced in accordance with the invention have the following qualities:

They can be easily wetted,
They disperse easily,
They remain in suspension well,
They do not foam excessively upon end use,
They do not form lumps over the course of storage, and
They do not cause degradation of the active material (which remains stable over time).

In order to demonstrate the desirable properties o the wettable powders of the invention, the following tests were carried out:

(1) Wettability: Determining the wetting time of a given amount of powder, using the method described in the CIPAC Handbook, page 967;

(2) Suspensivity: Defined as the amount of active material in suspension after a given period of time in a column of liquid of a given height, and expressed as a percentage of the amount of active material in the initial dispersion.

Two similar tests were used:
The test set forth in the CIPAC Handbook, page 861, The test described in FAO SPECIFICATIONS FOR PLANT PROTECTIONS PRODUCTS, 1971 edition (Food and Agriculture Organization of the United Nations), The test identified as WHO/SIF/1.4$_4$ (3) Formation of foams: The basic principle of the test, carried out in accordance with the method set forth in the CIPAC Handbook, page 955, consists of measuring the volume of foam obtained after agitation of a certain amount of powder introduced into a given volume of water.

The granules obtained in accordance with the invention have the following properties:
Very good dispersibility in water,
Good resistance to handling, without the formation of dust,
High proportion of active material,
Good physico-chemical stability,
Good fluidity.

In comparison to the wettable powders, they provide better dispersibility, a higher density and better safety, since there is no diffusion of dust into the atmosphere upon production and end use thereof.

The following tests were carried out in order to evaluate the properties of the granular material according to the invention:

(a) Apparent density:
The weight of 1 cm$^3$ of granules was determined by weighing $\phi$cm$^3$ of granules in a graduated test tube, without compacting;

(b) Granulometry:
Granulometry was determined by passing the material over a series of AFNOR standardized sieves, then weighing each granulometric fraction. It is expressed in terms of the mean diameter which is defined as being a diameter such that 50% by weight of the particles are of a diameter which is greater or smaller than the mean diameter;

(e) Resistance to attrition:
The granules to be tested, being larger than 500 μm in diameter, were subjected to a given mechanical treatment; agitation for one hour of the granules contained in a bottle which is half full.

Granulometric analysis was then carried out, permitting destruction of the granule to be evaluated. After that destruction test, the percentage of the fines was measured by passing the material through an AFNOR standardized sieve in which the mesh opening was 200 μm and the results obtained were compared to those measured before the test;

(d) Suspensivity:
Suspensivity was measured using the CIPAC method, as for the wettable powders, or using the method WHO/SIF/1.R$^4$;

(e) Dispersibility:
Dispersibility may be tested visually by pouring a number of granules into a test tube containing water. Another test consisted of measuring the flow time of an aqueous dispersion of granules over a sieve in which the mesh opening was 300 μm. One liter of an aqueous dispersion containing 20 g/l of granules of a diameter of from 200 to 1600 μm as prepared. The dispersion was poured into a funnel having a total height of 335 mm, a cone diameter of 180 mm and a cone height of 180 mm. The sieve was placed at the upper part of the stem of the funnel, 25 mm from the neck thereof, and its diameter (which was the inside diameter of the stem of the funnel) was 12 mm. The flow time of one liter of dispersion was measured. If logging was found, the amount of liquid which indeed flowed away was evaluated;

(f) Storage test:
Stability in storage was tested in an over using a cyclic procedure, for at least one month, the temperature varying from −5° C. to +45° C. The levels of performance were checked after the storage tests.

In order to further illustrate the present invention and the advantages thereof, the following specific examples are given, it being understood that same are intended only as illustrative and in nowise limitative. In said examples to follow, all parts and percentages are by weight, unless otherwise indicated.

EXAMPLE 1 and TESTS A and B:

EXAMPLE 1

Described hereinafter is the preparation of a wettable powder of technical D.D.T.

An air jet crusher was used to crush a technical D.D.T. (98% purity) until a powder was obtained, the particles of which had a mean diameter of 6 to 7 μm.

That active material was then mixed with silica and surface-active agents, the characteristics of which are set out below:

(a) ZEOSIL 39 A: precipitated silica having the following characteristics:

| (a) ZEOSIL 39 A: precipitated silica having the following characteristics: | | |
|---|---|---|
| (i) | BET surface area | 90 m$^2$/g |
| (ii) | Oil absorption | 280 cm$^3$ for 100 g |
| (iii) | Mean diameter of the particles | 20 μm |
| (iv) | Relative density | 1.9 |
| (v) | Apparent relative density | 0.25 |

(b) SOPROPON T 36, marketed by RHONE-POULENC: a maleic anhydride/diisobutylene copolymer having a mean molecular weight of about 10,000; a white powder containing 90% of dry solids and having a non-compacted relative density of 0.3 and a pH-value of 9.5±0.5, in 1% solution.

(c) SOPROPHOR DSS 11, marketed by RHONE-POULENC, which is a double sulfate of ammonium and di-(1-phenylethyl) phenol, in polyoxyethylenated form, having 7 moles of ethylene oxide per mole of phenol: brown viscous liquid.

(d) GEROPON 401 D, marketed by RHONE-POULENC or GERONAZZO, which is a polyoxyethylenated nonylphenol with 8.5 moles of ethylene oxide absorbed on silica.

The aforesaid components were used in amounts such as to provide a wettable powder having the following composition:

| (i) | Technical D.D.T. | 75.0% |
|---|---|---|
| (ii) | Silica (ZEOSIL 39 A) | 22.25% |
| (iii) | Maleic anhydride/diisobutylene copolymer (SOPROPON T36) | 0.5% |
| (iv) | Double sulfate of ammonium and di-(1-phenylethyl) phenol in polyoxyethylenated form (SOPROPHOR DSS 11) | 1.75% |
| (v) | Polyoxyethylenated nonylphenol (GEROPON 401 D) | 0.5% |

Tests A and B

By way of comparison, wettable powder of technical D.D.T. was prepared following the mode of operation of Example 1, but eliminating one of the constituents of the surface-active composition of the invention:

| | | |
|---|---|---|
| (i) | Technical D.D.T. | 75% |
| (ii) | Silica (ZEOSIL 39 A) | 20% |
| (iii) | Maleic anhydride/diisobutylene copolymer (SOPROPON T 36) | 2.5% |
| (iv) | Polyoxyethylenated nonylphenol (GEROPON 401 D) | 2.5% |

* in test B, the wettable powder had the following compositiob:

| | | |
|---|---|---|
| (i) | Technical D.D.T. | 75% |
| (ii) | Silica (ZEOSIL 39 A) | 20% |
| (iii) | Double sulfate of ammonium and di-(1-phenylethyl) phenol in polyoxyethylenated form (SOPROPHOR DSS 11) | 2.5% |
| (iv) | Polyoxyethylenated nonylphenol (GEROPON 401 D) | 2.5% |

The wettable powder obtained in accordance with the invention (Example 1) and the wettable powders of the comparative tests were subjected to the various tests set forth hereinafter.

TABLE I

| | Example 1 | Test A | Test B |
|---|---|---|---|
| Composition of the powders, in % | | | |
| Technical D.D.T. | 75.0 | 75.0 | 75.0 |
| Silica (ZEOSIL 39 A) | 22.25 | 20.00 | 20.0 |
| Maleic anhydride/diisobutylene copolymer (SOPROPON T 36) | 0.5 | 2.5 | 0 |
| Double sulfate of ammonium and di-(1-phenylethyl)phenol in polyoxyethylenated form (SOPROPHOR DDS 11) | 1.75 | 0 | 2.5 |
| Polyoxyethylenated nonylphenol (GEROPON 401 D) | 0.5 | 2.5 | 2.5 |
| Wettability, in seconds | 35.0 | 35.0 | 165 |
| Suspensivity | | | |
| FAO test, in % | 80 | 55 | 13 |
| WHO test, in % | 80 | 65 | 23 |
| Foams, in cm³ | 12 | 13 | 13 |

The results obtained are reported in the Table I which follows:

TABLE I

| | Example 1 | Test A | Test B |
|---|---|---|---|
| Composition of the powders, in % | | | |
| Technical D.D.T. | 75.0 | 75.0 | 75.0 |
| Silica (ZEOSIL 39 A) | 22.25 | 20.00 | 20.0 |
| Maleic anhydride/diisobutylene copolymer (SOPROPON T 36) | 0.5 | 2.5 | 0 |
| Double sulfate of ammonium and di-(1-phenylethyl)phenol in polyoxyethylenated form (SOPROPHOR DDS 11) | 1.75 | 0 | 2.5 |
| Polyoxyethylenated nonylphenol (GEROPON 401 D) | 0.5 | 2.5 | 2.5 |
| Wettability, in seconds | 35.0 | 35.0 | 165 |
| Suspensivity | | | |
| FAO test, in % | 80 | 55 | 13 |
| WHO test, in % | 80 | 65 | 23 |

TABLE I-continued

| | Example 1 | Test A | Test B |
|---|---|---|---|
| Foams, in cm³ | 12 | 13 | 13 |

Anaylsis of the data of Table I reveals:

(a) in test B, flocculation of the resultant suspension occurred;

(b) use of the composition of the invention made it possible to reduce the total amount of surface-active agents, while improving the quality of the formulation.

EXAMPLE 2 and TESTs C and D

EXAMPLE 2

This example describes preparing granules of technical tribunyl.

The active material was in a state of purity of 97.5% and was in micronized form, having a mean particle diameter of about 10 μm.

Using a fluidized bed granulator available under the trademark AEROMATIC TYPE STEA 1, the following materials were introduced into the bowl of the granulator:

(i) 143.6 g of technical tribunyl,
(ii) 24.4 g of kaolin,
(iii) 16 g of a maleic anhydride/diisobutylene copolymer (SOPROPON T 36),
(iv) 10 g of bentonite, marketed by CECA under the trademark CLARSOL FGN FR 4.

Homogenization of the mixture was carried out by means of a controlled, rising stream of air, at a substantial flow rate.

The mixture was then maintained in the fluidized state by a stream of preheated air at 30° C.

The following materials were sprayed over the mixture, over a period of 5 minutes:

(a) 100 g of water,
(b) 4 g of sodium dodecylbenzene sulfonate,
(c) 2 g of a double sulfate of ammonium and di-(1-phenylethyl)phenol in polyoxyethylenated form, having 7 moles of ethylene oxide per mole of phenol (SOPROPHOR DSS 7).

The sidewalls of the bowl were cleaned of clogging material thereon, if necessary, and the flow rate of the rising stream of air was adjusted in order to satisfactorily maintain the material in the fluidized state.

After agitation for 6 to 7 minutes, the granulation was terminated.

The granules were partially dried in the granulation bowl. For that purpose, the temperature of the rising stream of air was preset to about 70° C. for a period of 10 minutes: the temperature in the bowl was around 50° C. The drying operation was concluded by placing the material in a drying oven at a temperature of 50° C. for a period of 12 hours.

The granules were collected and then subjected to a sieving operation over a series of standardized sieves. 90% of the granules ranged from 200 to 1600 μm in size and therefore could be directly used for the application of the material.

The granules obtained had the following composition:

| | | |
|---|---|---|
| (i) | Technical tribunyl | 71.8% |
| (ii) | Maleic anhydride/diisobutylene copolymer (SOPROPON T 36) | 8.0% |
| (iii) | Double sulfate of ammonium and di-(1- | 1.0% |

-continued

| | | |
|---|---|---|
| | phenylethyl)phenol in polyoxyethylenated form (SOPROPHOR DSS 7) | |
| (iv) | Sodium dodecylbenzene sulfonate | 2.0% |
| (v) | Kaolin | 12.2% |
| (vi) | Bentonite (CLARSOL FGN FR4) | 5.0% |

Tests C and D

By way of comparison, the tribunyl granules were prepared following the mode of operation set forth in Example 2, but eliminating one of the constituents of the surface-active composition of the invention.

* test C, the granules had the following composition:

| | | |
|---|---|---|
| (i) | Technical tribunyl | 71.8% |
| (ii) | Maleic anhydride/diisobutylene copolymer (SOPROPON T 36) | 9.0% |
| (iii) | Sodium dodecylbenzene sulfonate | 2.0% |
| (iv) | Kaolin | 12.2% |
| (v) | Bentonite (CLARSOL FGN FR4) | 5.0% |

;ps * in test D, the granules had the following composition:

| | | |
|---|---|---|
| (i) | Technical tribunyl | 71.8% |
| (ii) | Double sulfate of ammonium and di-(1-phenylethyl)phenol in polyoxyethylenated form (SOPROPHOR DSS 7) | 9.0% |
| (iii) | Sodium dodecylbenzene sulfonate | 2.0% |
| (iv) | Kaolin | 12.2% |
| (v) | Bentonite (CLARSOL FGN FR4) | 5.0% |

In order to compare the properties of the granules of the invention (Example 2) and the granules of the comparative tests (Tests C and D), each was subjected to the various tests described above.

The results obtained are reported in Table II which follows:

TABLE II

| | Example 2 | Test C | Test D |
|---|---|---|---|
| Composition of the granules, in % | | | |
| Technical tribunyl | 71.8 | 71.8 | 71.8 |
| Maleic anhydride/diisobutylene copolymer (SOPROPON T 36) | 8.0 | 9.0 | 0 |
| Double sulfate of ammonium and di-(1-phenylethyl)phenol in polyoxyethylenated form (SOPROPHOR DSS 7) | 1.0 | 0 | 9.0 |
| Sodium dodecylbenzene sulfonate | 2.0 | 2.0 | 2.0 |
| Kaolin | 12.2 | 12.2 | 12.2 |
| Bentonite (CLARSOL FGN FR4) | 5.0 | 5.0 | 5.0 |
| Apparent relative density | 0.8 | 0.8 | 0.8 |
| Resistance to attrition | <1% | <1% | <1% |
| Dispersibility | | | |
| quantity which flows away | 1000 cm³ | 200 cm³ | 100 cm³ |
| flow time | 12 s. | * | * |
| Suspensivity (WHO test) | 90% | 63% | 10% |

*Clogging of the filter

Table II clearly evidences he synergistic effect achieved by using the surface-active composition of the invention in the formulation of an active material in the form of granules, in regard to their dispersibility and suspensivity properties.

EXAMPLE 3 and TESTs E AND F

EXAMPLES 3

This example describes the formulation of phenmediphame in the form of granules: the active material was micronized and had a mean diameter of 6 to 7 μm.

The following materials were introduced into the bowl of a mixer-granulator of the type ROWENTA MULTIXER:

(i) 80 g of phenmediphame, (ii) 8 g of a surface-active composition in the form of a powder containing 7.2 g of a maleic anhydride/diisobutylene copolymer (SOPROPON T 36) and 0.8 g of a double sulfate of ammonium and di-(1-phenylethyl)phenol in polyoxyethylenated form (SOPROPHOR DSS 7), (iii) 3 g of bentonite (CLARSOL FGN FR4), These powders were mixed for 3 to 4 minutes, followed by the rapid addition of the following:

(iv) 10 g of water, (v) 2 g of sodium dodecylbenzene sulfonate.

The mixture was maintained in an agitated condition, with the sidewalls of the bowl being cleaned of clogging material, if necessary.

The following materials were then added slowly: - 10 g of water.

After 5 to 6 minutes in total, the granulation operation was terminated. The granules were dried for 12 hours in a drying oven at 50° C. and the granules obtained had the following composition:

| | | |
|---|---|---|
| (i) | Phenmediphame | 80% |
| (ii) | Maleic anhydride/diisobutylene copolymer (SOPROPON T 36) | 7.2% |
| (iii) | Double sulfate of ammonium and di-(1-phenylethyl)phenol in polyoxyethylenated form (SOPROPHOR DSS 7) | 0.8% |
| (iv) | Sodium dodecylbenzene sulfonate | 2.0% |
| (v) | Kaolin | 7.0% |
| (vi) | Bentonite (CLARSOL FGN FR4) | 3% |

Tests E and F

Comparative tests were carried out, in regard to the preparation of granules using only the maleic anhydride/diisobutylene copolymer in Test E and the double sulfate of ammonium and di-(1-phenylethyl)phenol in polyoxyethylenated form, in Test F.

A check was made in respect of the suspensivity achieved with the granules of Example 3 and Tests E and F.

The results obtained are reported in Table III which follows:

TABLE III

| | Example 3 | Test E | Test F |
|---|---|---|---|
| Composition of the granules, in % | | | |
| Phenmediphame | 80 | 80 | 80 |
| Maleic anhydride/diisobutylene copolymer (SOPROPON T 36) | 7.2 | 8.0 | 0 |
| Double sulfate of ammonium and di-(1-phenylethyl)phenol in polyoxyethylenated form (SOPROPHOR DSS 7) | 0.8 | 0 | 8.0 |
| Sodium dodecylbenzene sulfonate | 2.0 | 2.0 | 2.0 |
| Kaolin | 7.0 | 7.0 | 7.0 |
| Bentonite (CLARSOL FGN FR4) | 3.0 | 3.0 | 3.0 |

TABLE III-continued

|  | Example 3 | Test E | Test F |
|---|---|---|---|
| Suspensivity (WHO test) | 87.5 | 77 | 50 |

EXAMPLE 4 and TESTS G and H

Example 4

Granules of technical atrazine (90% plurality) were prepared according to the procedure described in Example 3. The surface-active composition used included a maleic anhydride/diisobutylene copolymer (SORPROPON T 36) and a phosphat of di-(1-phenylethyl)-phenol, which was in polyoxyethlenated form, with 16 moles of ethylene oxide per mole of phenol, and neutralized with triethanolamine.

By way of comparison (Tests G and H), granules of atrazine were prepared, while eliminating one of the constituents of the surface-active composition of the invention.

The composition of the granules of Example 4 and Tests G and H, as well as the results obtained in the suspensivity test, are reported in Table IV which follows:

TABLE IV

|  | Example 4 | Test G | Test H |
|---|---|---|---|
| Composition of the granules, in % |  |  |  |
| Technical atrazine | 92 | 92 | 92 |
| Maleic anhydride/ diisobutylene copolymer (SOPROPON T 36) | 6 | 7 | 0 |
| Phosphate of di-(1-phenylethyl)phenol which was polyoxyethylenated and neutralized (SOPROPHOR FL) | 1 | 0 | 7 |
| Sodium dodecylbenzene sulfonate | 1 | 1 | 1 |
| Suspensivity (WHO test) | 93% | 82% | * |

*Granulation impossible

The granules obtained in accordance with the invention enjoy improved suspensivity, which demonstrates the good dispersibility properties of the composition of the invention.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A surface-active, storage-stable composition of matter containing at least one material of limited solubility of dispersibility, including a first surface-active agent (a) comprising at least one copolymer of (i) an olefinically unsaturated monomer having the formula (I):

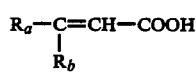
$$R_a-C=CH-COOH \quad (I)$$
with $R_b$ below $R_a-C$.

or carboxyl derivative thereof, wherein $R_a$ is hydrogen, an alkyl radical having from 1 to 10 carbon atoms, or a carboxylated such radical, and $R_b$ is a carboxyl group, with (ii) an olefinically unsaturated comonomer copolymerizable therewith and having one of the formulae (II) and/or (III):

wherein $R_c$ is hydrogen or a straight or branched chain alkyl radical having from 1 to 4 carbon atoms, $R_d$ is a straight or branched head chain alkyl radical having from 1 to 12 carbon atoms, $R_e$ is hydrogen or an alkyl radical having from 1 to 4 carbon atoms, and $R_f$ is:

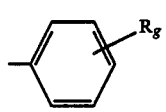

wherein $R_g$ is hydrogen or an alkyl radical having from 1 to 4 carbon atoms;—Cl; OOC-$R_h$, wherein $R_h$ is an alkyl radical having from 1 to 8 carbon atoms; —O-$R_i$, wherein $R_j{=}_{50}R_h$; —CO—OH; —COO—$R_j$, wherein $R_i{=}R_h$; —COOH; —COO—$R_j$, wherein $R_j{=}R_h$; —CO—NH$_2$; or —C N, and wherein the molar ratio of the components of formula (I) to the compounds of formula (II) and/or (III) is approximately one, and a second surface-active agent (b) comprising at least one mixed sulfate having the formula (IV) and/or phosphate ester having the formula (V):

wherein n ranges from 1 to 80, M is a solubilizing radical, $M_1$ is hydrogen or M, R is an alkylene radical having from 2 to 4 carbon atoms, $R_2$ is $M_1$ or the radical $R_1$-(-O—R-)$_n$- and $R_1$ is a radical having the formula (VI):

wherein m is an integer ranging form 1 to 3, p is 1 or 2, $R_4$ is hydrogen or an alkyl radical having from 1 to 4 carbon atoms, and $R_3$ is a radical having the formula (VII):

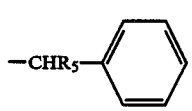

wherein $R_5$ is hydrogen, an alkyl radical having from 1 to 4 carbon atoms, or a phenyl radical, and wherein said surface-active agent (b) is present in an amount effective to enhance dispersability or solubility of said at least one material contained therein as compared to its dispersibility or solubility when (a) or (b) are used alone.

2. The surface-active composition as defined by claim 1, said monomer (i) comprising maleic or fumaric acid, or ester or hemiester thereof, itaconic or citraconic acid, maleic anhydride, mono- or dialkylmaleic acid or mono- or dialkylfumaric acid, the alkyl moieties of which having from 1 to 4 carbon atoms.

3. The surface-active composition as defined by claim 1, said copolymer (a) comprising a straight or branched chain unsaturated hydrocarbon comonomer (II) having from 2 to 8 carbon atoms.

4. The surface-active composition as defined by claim 3, said comonomer (II) comprising ethylene, propylene, but-1-ene, isobutylene, n-pent-1-ene, isoprene, 2-methyl-but-1-ene, n-hex-1-ene, 2-methyl-pent-1-ene, 4-methyl-pent-1-ene, 2-ethyl-but-1-ene, diisobutylene, 1,3-butadiene, 1,3pentadiene, 1,3-hexadiene, 1,3-octadiene, 2-methyl-3,3- dimethyl-pent-1-ene or 2-methyl-4,4-dimethyl-pent-1-ene.

5. The surface-active composition as defined by claim 1, said copolymer (a) comprising a vinyl comonomer (III).

6. The surface-active composition as defined by claim 1, said copolymer (a) comprising styrene, vinyl chloride, a vinyl ester of an aliphatic acid having from 1 to 8 carbon atoms, a vinyl ether, acrylic or methacrylic acid, or alkyl ester having from 1 to 8 carbon atoms, acrylamide, methacrylamide, acrylonitrile or methacrylonitrile.

7. The surface-active composition as defined by claim 1, said copolymer (a) comprising a maleic anhydride/diisobutylene copolymer.

8. The surface-active composition as defined by claim 1, said copolymer (a) having a molecular weight ranging from 500 to 50,000.

9. The surface-active composition as defined by claim 8, said copolymer (a) having a molecular weight ranging from 500 to 15,000.

10. The surface-active composition as defined by claim 1, wherein said copolymer (a), the molar ratio of monomer (i) to comonomer (II) and/or (III) is about 1.

11. The surface-active composition as defined by claim 1, said copolymer (a) having been neutralized to a pH of from about 8 to 12.

12. The surface-active composition as defined by claim 1, wherein said mixed sulfate (IV) and/or phosphate ester (V), n ranges from 1 to 40, M is an alkali metal or ammonium residue of the formula $-N(R_6R_7R_8R_9)$, in which $R_6$ is hydrogen and $R_7$, $R_8$ and $R_9$, which may be identical or different, are each hydrogen, alkyl or hydroxyalkyl, with the proviso that two of such alkyl radicals may together form a single divalent radical which may contain an oxygen bridge and the total number of carbon atoms therein ranging from 1 to 6, $M_1$ is hydrogen or M, m is 2 or 3, $R_4$ is hydrogen, and $R_5$ is hydrogen, methyl or phenyl.

13. The surface-active composition as defined by claim 12, wherein D ranges from 3 to 40, and M is sodium, potassium, ammonium, monoethanolamine, diethanolamine or triethanolamine.

14. The surface-active composition as defined by claim 12, wherein R is ethylene.

15. The surface-active composition as defined by claim 1, said second surface-active agent (b) comprising a sulfate of tri-(1-phenylethyl)phenols, in polyoxyethylenated form, having from 10 to 40 moles of ethylene oxide per mole of phenol, in acid or neutralized form, a sulfate of di-(1-phenylethyl)phenols, in polyoxyethylenated form, having from 3 to 20 moles of ethylene oxide per mole of phenol, in acid or neutralized form, a phosphate of tri-(1-phenylethyl)phenols, in polyoxyethylenated form, having from 10 to 40 moles of ethylene oxide per mole of phenol, in acid or neutralized form, or a phosphate of di-(1-phenylethyl)phenols in polyoxyethylenated form, having from 3 to 20 moles of ethylene oxide per mole of phenol, in acid or neutralized form.

16. The surface-active composition as defined by claim 1, comprising from 10 to 90% by weight of said at least one surface-active agent (a) and from 90 to 10% by weight of said at least one surface-active agent (b).

17. The surface-active composition as defined by claim 16, comprising from 10 to 30% by weight of said at least one surface-active agent (a) and from 90 to 70% by weight of said at least one surface-active agent (b).

18. The surface-active composition as defined by claim 16, comprising from 80 to 90% by weight of said at least one surface-active agent (a) and from 20 to 10% by weight of said at least one surface-active agent (b).

19. The surface-active composition as defined by claim 1, formulated in liquid form.

20. The surface-active composition as defined by claim 1, formulated in solid form.

21. The surface-active composition as defined by claim 20, formulated in powder form.

22. The surface-active composition as defined by claim 20, formulated in granular form.

23. The surface-active composition as defined by claim 1, further comprising a difficultly soluble active agent.

24. The surface-active composition as defined by claim 23, comprising a biocidal active agent.

25. The surface-active composition as defined by claim 23, formulated as a wettable powder.

26. The surface-active composition as defined by claim 23, formulated in granular form.

27. The surface-active composition as defined by claim 23, further comprising an inert filler material.

28. The surface-active composition as defined by claim 23, further comprising a wetting agent.

29. The surface-active composition as defined by claim 28, said wetting agent comprising an anionic or nonionic surfactant.

30. The surface-active composition as defined by claim 23, comprising a hydrophobic active agent.

31. The surface-active composition as defined by claim 23, further comprising an auxiliary additive.

32. The surface-active agent as defined by claim 23, wherein said active agent is in liquid form absorbed onto particulate carrier therefor.

33. The surface-active composition as defined by claim 24, formulated as a wettable powder.

34. The surface-active composition as defined by claim 24, formulated in granular form.

35. A stable, homogeneous liquid suspension of the surface-active composition as defined by claim 23.

36. The stable suspension as defined by claim 35, comprising a homogeneous aqueous dispersion.

37. The surface-active composition as defined by claim 23, further comprising a dispersing aid.

38. An aqueous or organic liquid slurry of the surface-active composition as defined by claim 23.

39. The surface-active composition as defined by claim 23, said active agent comprising a pigment, filler, colorant, optical bluing agent, plastics additive, paint additive, textile additive, concrete additive or cosmetic additive.

40. The surface-active composition as defined by claim 24, said biocidal active agent comprising an insecticide, acaricide, fungicide, herbicide, nematicide or rodenticide.

41. The surface-active composition as defined by claim 23, said active agent comprising an insect attractant or repellent.

* * * * *